US011024404B2

(12) United States Patent
Mihalef et al.

(10) Patent No.: US 11,024,404 B2
(45) Date of Patent: Jun. 1, 2021

(54) SYSTEM AND METHOD FOR MEDICAL IMAGE BASED CARDIO-EMBOLIC STROKE RISK PREDICTION

(71) Applicant: Siemens Healthcare GmbH, Erlangen (DE)

(72) Inventors: Viorel Mihalef, North Brunswick, NJ (US); Puneet Sharma, Pheasant Run, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 548 days.

(21) Appl. No.: 15/424,911

(22) Filed: Feb. 6, 2017

(65) Prior Publication Data

US 2017/0255745 A1 Sep. 7, 2017

Related U.S. Application Data

(60) Provisional application No. 62/301,861, filed on Mar. 1, 2016.

(51) Int. Cl.
*G16H 10/60* (2018.01)
*G16H 50/50* (2018.01)
(Continued)

(52) U.S. Cl.
CPC ............ *G16H 10/60* (2018.01); *G06F 17/11* (2013.01); *G06T 7/12* (2017.01); *G06T 7/149* (2017.01);
(Continued)

(58) Field of Classification Search
CPC ........ G06F 19/321; G06F 17/11; G06T 7/149; G06T 7/12; G06T 2207/30048;
(Continued)

(56) References Cited

U.S. PATENT DOCUMENTS

| 7,747,047 B2 | 6/2010 | Okerlund et al. |
| 7,916,919 B2 | 3/2011 | Zheng et al. |

(Continued)

FOREIGN PATENT DOCUMENTS

| CN | 1550224 B | 4/2010 |
| CN | 103646135 A | 3/2014 |
| WO | WO2008049125 A3 | 7/2008 |

OTHER PUBLICATIONS

Takehiro Kimura, MD, PhD et al., Anatomical characteristics of the left atrial appendage in cardiogenic stroke with low CHADS2 scores, Jun. 2013, Heart Rhythm vol. 10, Issue 6, pp. 921-925 (Year: 2013).*

(Continued)

*Primary Examiner* — Fonya M Long
*Assistant Examiner* — Kimberly A. Sass (57) ABSTRACT

A system and method for medical image based patient-specific ischemic stroke risk prediction is disclosed. Left atrium (LA) and left atrium appendage (LAA) measurements are extracted from medical image data of a patient. Derived metrics for the LA and LAA of the patient are computed using a patient-specific computational model of cardiac function based on the LA and LAA measurements extracted from the medical image data of the patient. A stroke risk score for the patient is calculated based on the extracted LA and LAA measurements and the computed derived metrics for the LA and LAA of the patient using a trained machine learning based classifier, which inputs the extracted LA and LAA measurements and the computed derived metrics for the LA and LAA as features.

32 Claims, 5 Drawing Sheets

(51) Int. Cl.
  *G06T 7/12* (2017.01)
  *G06T 7/149* (2017.01)
  *G16H 30/20* (2018.01)
  *G06F 17/11* (2006.01)
  *G06N 7/00* (2006.01)
  *G06N 3/08* (2006.01)

(52) U.S. Cl.
  CPC .............. *G16H 30/20* (2018.01); *G16H 50/50* (2018.01); *G06N 3/08* (2013.01); *G06N 7/005* (2013.01); *G06T 2207/20081* (2013.01); *G06T 2207/30048* (2013.01)

(58) Field of Classification Search
  CPC .......... G06T 2207/20081; G16H 50/50; G16H 10/60; G06N 7/005; G06N 3/08
  USPC ............................................................ 705/3
  See application file for complete search history.

(56) References Cited

U.S. PATENT DOCUMENTS

| | | | |
|---|---|---|---|
| 8,644,576 | B2 | 2/2014 | Zheng et al. |
| 8,682,626 | B2 | 3/2014 | Ionasec et al. |
| 8,724,881 | B2 | 5/2014 | Zheng et al. |
| 10,354,758 | B2 | 7/2019 | Yang et al. |
| 2010/0040272 | A1 | 2/2010 | Zheng et al. |
| 2010/0070249 | A1 | 3/2010 | Ionasec et al. |
| 2011/0166618 | A1* | 7/2011 | Zhang .................... G16H 40/63 607/28 |
| 2011/0257545 | A1 | 10/2011 | Suri |
| 2012/0022843 | A1 | 1/2012 | Ionasec et al. |
| 2013/0226542 | A1 | 8/2013 | Rapaka et al. |
| 2014/0071125 | A1* | 3/2014 | Burlina ................... G06T 17/00 345/420 |
| 2014/0142060 | A1* | 5/2014 | Stein ..................... C12Q 1/6883 514/52 |
| 2016/0058520 | A1 | 3/2016 | Yang et al. |

OTHER PUBLICATIONS

Yefeng Zheng*, Dong Yang, Matthias John, and Dorin Comaniciu, Multi-Part Modeling and Segmentation of Left Atrium in C-Arm CT for Image-Guided Ablation of Atrial Fibrillation, Februrary 2014, IEEE Transactions on Medical Imaging, vol. 33, No. 2 (Year: 2014).*

Peyrat et al., "A Computational Framework for the Statistical Analysis of Cardiac Diffusion Tensors: Application to a Small Database of Canine Hearts," IEEE Transactions on Medical Imaging, 2007, vol. 26, No. 11, pp. 1500-1514.

Yang et al., "Data-Driven Model Reduction for Fast, High Fidelity Atrial, Electrophysiology Computations," Functional Imaging and Modeling of the Heart, LNCS 9126, 2015, pp. 466-474.

Koizumi et al., "Numerical Analysis of Hemodynamic Changes in the Left Atrium Due to Atrial Fibrillation," Journal of Biomechanics, 2015, vol. 48, No. 3, pp. 472-478.

First Office Action dated Nov. 5, 2019 in corresponding Chinese Patent Application No. 201710116719.5.

Office Action dated Jun. 29, 2020 in corresponding Chinese Patent Application No. 201710116719.5.

Freeman et al.,"Stroke Prevention in Atrial Fibrillation and Other Major Cardiac Sources of Embolism", Neurologic Clinics, vol. 26, No. 4, Nov. 2008, pp. 1129-1160.

Freeman et al., "Prevention of Cardioembolic Stroke", Neurotherapeutics, Jun. 3, 2011, vol. 8, pp. 488-502.

Haissaguerre et al., "Atrial Fibrillatory Cycle Length: Computer Simulation and Potential Clinical Importance", Europace, Nov. 2007, pp. vi64-vi70.

Leithäuser et al., "Rheological and Hemostasiological Aspects of Thrombus Formation in the Left Atrial Appendage in Atrial Fibrillation? a New Strategy for Prevention of Cardioembolic Stroke", Clinical Hemorheology and Microcirculation, vol. 45, 2010, pp. 311-323.

Mihalef et al., "Patient-Specific Modelling of Whole Heart Anatomy, Dynamics and Haemodynamics from Four-Dimensional Cardiac CT Images", Interface Focus, vol. 1, No. 3, 2011, pp. 286-296.

Verheule et al., "Increased Vulnerability to Atrial Fibrillation in Transgenic Mice with Selective Atrial Fibrosis Caused by Dverexpression of TGF-β1", Journal of the American Heart Association, Circulation Research, vol. 94, No. 11, 2004, pp.1458-1465.

Wessler et al., "Controversies in Cardioembolic Stroke", Current Treatment Options in Cardiovascular Medicine, 2015, vol. 17, No. 358, pp. 1-12.

Yamamoto et al., "Complex Left Atrial Appendage Morphology and Left Atrial Appendage Thrombus Formation in Patients with Atrial Fibrillation", Circulation Cardiovascular Imaging, vol. 7, No. 2, Mar. 2014, pp. 337-343.

Rapaka et al., "LBM-EP: Lattice-Boltzmann Method for Fast Cardiac Electrophysiology Simulation from 3D Images", Medical Image Computing and Computer Assisted Intervention MICCAI 2012, vol. 7511, Springer Berlin Heidelberg, 2012, pp. 33-40.

Zheng et al., "Four-Chamber Heart Modeling and Automatic Segmentation for 3D Cardiac CT Volumes Using Marginal Space Learning and Steerable Features", IEEE Transactions on Medical Imaging, 2008, 14 pgs.

Yang et al., "3D Ultrasound Tracking of the Left Ventricles Using One-Step Forward Prediction and Data Fusion of Collaborative Trackers", Proc. IEEE CVPR. 2008, 8 pgs.

Zheng et al., "Automatic Left Ventricle Detection in MR Images Using Marginal Space Learning and Component-Based Voting," SPIE Medical Imaging, Orlando, FL, 2009, 12 pgs.

Zheng et al., "Precise Segmentation of the Left Atrium in C-Arm CT Volumes with Applications to Atrial Fibrillation Ablation," Proceedings of ISBI 2012, 4 pgs.

Schneck et al., "Cardioembolic Stroke", Medscape, http://emedicine.medscape.com/article/1160380-overview#a2, May 20, 2020, 3 pgs.

Zheng et al., "Fast Automatic Heart Chamber Segmentation from 3D CT Data Using Marginal Space Learning and Steerable Features", IEEE ICCV, 2007, 8 pgs.

Office Action dated Sep. 14, 2020 in corresponding German Patent Application No. 10 2017 203 299.5.

Wikipedia:"CHA2DS2-VASc Score—Versionsunterschied"; www.wikipedia.de "CHA2DS2-VASc Score"—Version dated Sep. 19, 2016; pp. 1-5; https://de.wikipedia.org/w.-index.php?title=CHA2DS2-VASc_Score&oldid=158040640.

* cited by examiner

SYSTEM AND METHOD FOR MEDICAL IMAGE BASED CARDIO-EMBOLIC STROKE RISK PREDICTION

This application claims the benefit of U.S. Provisional Application No. 62/301,861, filed Mar. 1, 2016, the disclosure of which is herein incorporated by reference in its entirety.

BACKGROUND OF THE INVENTION

The present invention relates to patient-specific stroke risk prediction, and more particularly to medical image based patient-specific cardio-embolic stroke risk prediction.

Stroke is the fifth leading cause of death and the leading cause of adult disability in the United States. There are two types of strokes, hemorrhagic and ischemic, with approximately 13% of strokes that occur being hemorrhagic and 87% being ischemic. Ischemic strokes can in turn be embolic (~20%) or thrombotic (~80%) type. In an embolic stroke, a blood clot or plaque fragment forms somewhere in the body (usually the heart) and travels to the brain, where it blocks a small vessel. In a thrombotic stroke, the blood clot forms inside an artery that supplies blood to the brain.

Embolic strokes are disproportionately more disabling than non-embolic stokes due to occlusion of larger intracranial arteries and larger ischemic brain volume. It has been estimated that 45-50% of embolic strokes occur in hearts with atrial fibrillation (Afib). Furthermore, it has been estimated that approximately 2.3 to 3.2 million people were affected with Afib in the United States in 2011, and based on epidemiologic data, the future projections of patient with Afib could exceed 12 million by 2050.

The current clinical practice regarding risk prediction for cardio-embolic stroke patients is extensive and includes a detailed history, physical examination (including cardiac auscultation for murmurs and assessment for an irregular heart rhythm), neuroimaging, electrocardiogram, and laboratory and echocardiographic data. However, the risk indices extracted from such evaluations are limited to simple statistical indicators with large variances, usually based on clinical longitudinal data. There are a number of disadvantages to this approach to risk prediction, including the time plasticity (i.e., uncertainty) and the large range of these indices, as well as weak/reduced patient specificity.

BRIEF SUMMARY OF THE INVENTION

The present invention provides a method and system for patient-specific prediction of ischemic stroke risk. Embodiments of the present invention provide ischemic stroke risk prediction based on an automated analysis of the left atrium (LA) and the left atrium appendage (LAA).

In one embodiment of the present invention, left atrium (LA) and left atrium appendage (LAA) measurements are extracted from medical image data of a patient. Derived metrics for the LA and LAA of the patient are computed using a patient-specific computational model of cardiac function based on the LA and LAA measurements extracted from the medical image data of the patient. A stroke risk score for the patient is calculated based on the extracted LA and LAA measurements and the computed derived metrics for the LA and LAA of the patient using a trained machine learning based classifier, wherein the extracted LA and LAA measurements and the computed derived metrics for the LA and LAA are input as features to the trained machine learning based classifier.

These and other advantages of the invention will be apparent to those of ordinary skill in the art by reference to the following detailed description and the accompanying drawings.

DETAILED DESCRIPTION

The present invention relates to patient-specific ischemic stroke risk prediction based on an automated analysis of the left atrium (LA) and left atrial appendage (LAA) in medical images. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system or available through a network system.

Embodiments of the present invention provide ischemic stroke risk prediction for a patient based on an automated analysis of the LA and LAA. While atrial fibrillation, atrial flutter, sinus node dysfunction/atrial asystole, arrhythmias, atrial septal aneurysms, and the Chiari network are all associated with left atrial thrombi, the LAA is considered to be the primary formation site. The mechanism for such formation involves stagnation of blood in the LAA due to inefficient blood evacuation, associated for example with pathological contraction patterns. Embodiments of the present invention provide patient-specific ischemic (cardio-embolic) stroke risk stratification using biomarkers based on features associated with the LAA, as well as "exogenic" biomarkers including type of medication. The features associated with the LAA can include morphological features, hemodynamic features, and "hidden" variables detected by a machine learning algorithm. Embodiments of the present invention rely on computational modeling to reveal various factors that play a role in LAA thrombus formation and the eventual risk of embolic stroke. Embodiments of the present invention utilize patient-specific anatomical and computational modeling to determine well-known risk factors of LAA thrombus formation, including the CHADS2 score, LA volume, left ventricular ejection fraction (LVEF), and degree of dense spontaneous echo contrast (SEC), as well as new factors of interest including LAA morphology complexity (e.g., number of LAA lobes) and relative residence time (RRT).

Figure 1:
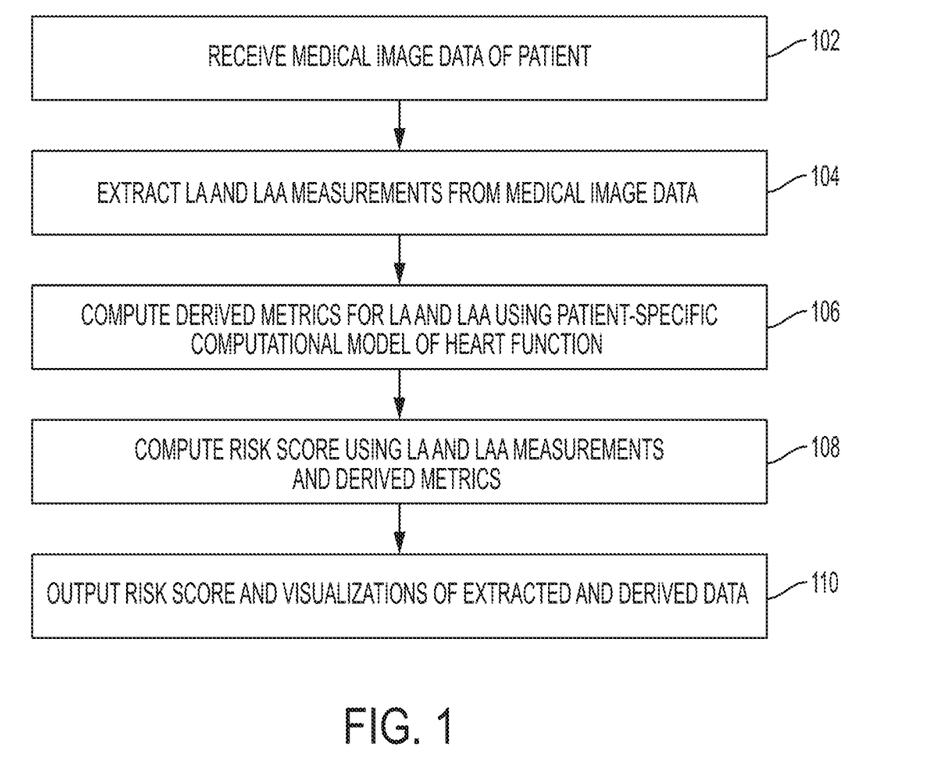
FIG. 1 illustrates a method of medical image based patient-specific ischemic stroke risk prediction according to an embodiment of the present invention.

FIG. 1 illustrates a method of medical image based patient-specific ischemic stroke risk prediction according to an embodiment of the present invention. At step 102, medical image data of a patient is received. The medical image data can be acquired using any type of medical imaging modality, such as magnetic resonance imaging (MRI), computed tomography (CT), C-arm CT (DynaCT), 3D echocardiogram (echo), three-dimensional rotational angiography, ultrasound (US), etc., provided that the heart is visible in the medical image data. In an advantageous implementation, the medical image data includes three dimensional (3D) and/or 4D (3D+time) medical image data. The medical image data can be received directly from an image acquisition device, such as an MRI scanner, a CT scanner, a C-arm image-acquisition device, or an US scanner, or the medical image data can be received by loading previously stored medical image data of the patient. In addition to medical image data, clinical measurements of the patient may also be received. For example, clinical data such as electrocardiogram (ECG) measurements and/or pressure cuff measurements of the patient can be received. EP features such as coarse fibrillatory waves, atrial flutter, and/or multifocal atrial tachycardia (MAT), can be extracted from ECG measurements of the patient.

Figure 2:
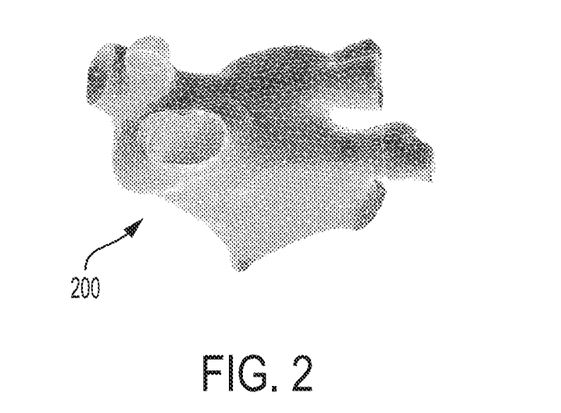
FIG. 2 illustrates an exemplary triangular mesh of a left atrium (LA) segmented from CT data.

At step 104, LA and LAA measurements are extracted from the medical image data of the patient. In particular, patient-specific anatomy/morphology of the LA and the LAA can be extracted from the medical image data of the patient by generating a patient-specific anatomical model of the LA. In order to generate a patient-specific anatomical model of the LA, the medical image data (e.g., 3D echo, MRI, CT, DynaCT) is used to generate a segmentation of the LA, represented either explicitly as a mesh (e.g., triangular mesh), or implicitly, for example by a signed or unsigned distance function, or a level set. FIG. 2 illustrates an exemplary triangular mesh 200 of an LA segmented from CT data. A single mesh corresponding to a given time stamp can be generated, or a sequence of meshes covering part or all of the cardiac cycle can be generated, thus capturing the wall motion of the LA. In a possible implementation only the LA is segmented in the medical image data. In other possible implementations, a more complete segmentation of the left heart (i.e., LA and left ventricle) or a segmentation of the whole may be generated. In addition to the anatomy/morphology of the patient, other LA and LAA measurements, such as hemodynamics or electrophysiology information may also be extracted. For example, hemodynamics information, such as blood flow velocity measurements can be extracted from Doppler echo images and/or phase contrast MRI (PC-MRI) images of the patient. Electrophysiology (EP) measurements can be extracted from an ECG of the patient and by personalizing a computational EP model for the patient. Nerves and/or fibers in the LA can be modeled as part of the anatomical model of the LA.

Figure 3A:
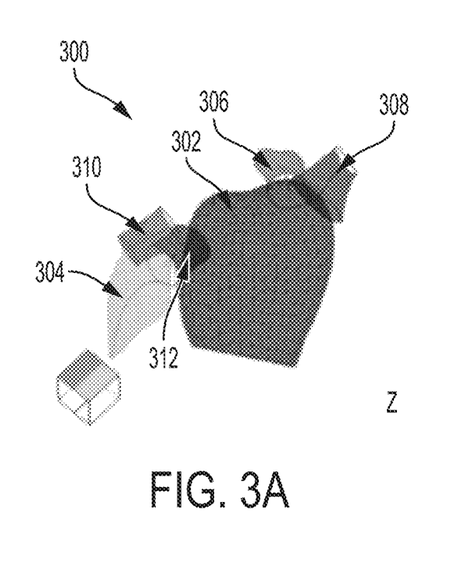
FIG. 3 illustrates a part-based left atrium (LA) model according to an embodiment of the present invention.
Figure 3B:
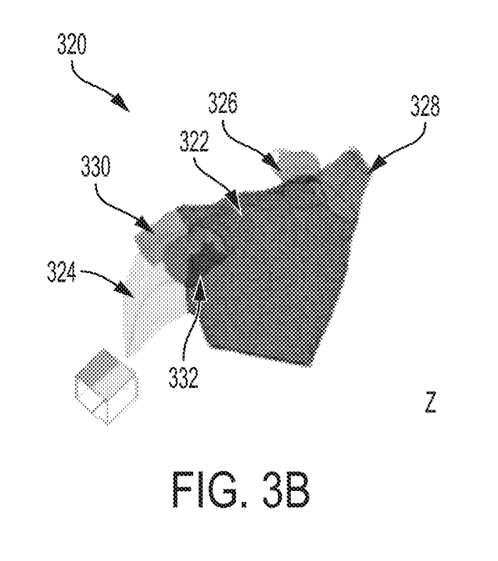

In an advantageous embodiment, an anatomical model of the LA can be generated by segmenting the LA in the medical image data using a multi-part atrial model. FIG. 3 illustrates a part-based left atrium (LA) model according to an embodiment of the present invention. As shown in image (a) of FIG. 3, the part-based LA model 300 includes the LA chamber body 302, left atrial appendage (LAA) 304, and four major pulmonary veins (PVs) 306, 308, 310, and 312. The four major PVs are the left inferior PV 312, the left superior PV 310, the right inferior PV 308, and the right superior PV 306. The shape of the LAA 304 is close to a tilted cone and the PVs 306, 308, 310, and 312 each have a tubular structure. Each LA part 302, 304, 306, 308, 310, and 312 is a much simpler anatomical structure as compared to a holistic LA structure, and therefore can be detected and segmented using a model based approach. According to an advantageous embodiment, the LA chamber body 302 and LAA 304 can be segmented first together using a Marginal Space Learning (MSL) framework. The idea of MSL is not to learn a monolithic classifier directly in the full similarity transformation parameter space but to incrementally learn classifiers on marginal spaces. In particular, the detection of each heart chamber can be split into three problems: position estimation, position-orientation estimation, and position-orientation-scale estimation. A separate classifier is trained based on annotated training data for each of these estimation problems. Each classifier can be a probabilistic boosting tree (PBT) classifier trained based on annotated training data. The classifiers in the lower dimensional marginal spaces are used to prune the searching space efficiently. This object localization stage results in an estimated transformation (position, orientation, and scale) of the object (e.g., heart chamber). After automatic object localization, the mean shape model of the object is aligned with the estimated transformation to get a rough estimate of the object shape. The shape is then deformed locally to fit the object boundary. Active shape models (ASM) can be used to deform an initial estimate of a non-rigid shape under the guidance of the image evidence and the shape prior. However, a non-learning based generic boundary detector, as used in conventional ASM applications, does not work effectively in heart chamber deformation due to the complex background and weak edges. Instead, a learning based boundary detector can be used to exploit more image evidences to achieve a robust boundary detection. Additional details regarding MSL-based heart chamber segmentation are described in U.S. Pat. No. 7,916,919, issued Mar. 29, 2011, and entitled "System and Method for Segmenting Chambers of a Heart in a Three Dimensional Image", United States Published Patent Application No. 2010/0040272, and United States Published Patent Application No. 2012/0022843, which are incorporated herein by reference. Once the LA chamber body 302 and LAA 304 are segmented, the remaining LA parts 306, 308, 310, and 312 are segmented using MSL-based segmentation subject to a statistical shape constraint based on the segmented LA chamber body 302.

Once the LA parts are segmented in the medical image data, they are combined into a consolidated mesh model. Image (b) of FIG. 3 shows a consolidated LA mesh 320 including the LA chamber 322, LAA 324, and PVs 326, 328, 330, and 332. Additional details regarding methods for part-based atrial segmentation are described in U.S. Pat. No. 8,644,576 and U.S. Pat. No. 8,724,881, which are incorporated herein by reference in their entirety. In a possible implementation, the right atrium (RA) can also be segmented similarly either holistically or using a part-based method using MSL-based segmentation, and the LA and RA models can be combined into a bi-atrial mesh. Atrial anatomical structures, such as the SA node, Bachmann's bundle (BB), crista terminalis, and pectinate muscles (PM), can be tagged on the mesh vertices of the atrial mesh.

A fiber orientation for the LA can be modeled based on historical observations. In a possible implementation, it can be assumed that the atrial tissue is isotropic and propagation is equally likely in all directions. Alternatively, if in-vivo diffusion tensor (DT) MR images are available, DT MR images of the patient's cardiac fibers can be directly mapped to the anatomical model through image registration. In this case, the DT MR image is non-linearly registered to the medical image in which the LA model is segmented. The resulting transformation is used to deform the tensor field in the DT MR image towards the anatomical model. The Finite Strain method, the details of which are described in Peyrat et al., "A Computational Framework for the Statistical Analysis of Cardiac Diffusion Tensors: Application to a Small Database of Canine Hearts", *IEEE TMI*, 26(11):1500-1514, 2007, which is incorporated herein by reference, can be used to reorient the tensors once the tensors are registered to the anatomical model. It is also possible, that an atlas of fiber architecture is available and the atlas is registered to the patient-specific anatomical LA model using standard image registration techniques.

Local atrial wall thickness is non-uniform with values ranging between 0.8 mm and 3 mm. Regional atrial wall thickness can be extracted from high resolution MRI images, but it can be time-consuming the extract the atrial wall thickness for the whole atrium. An alternative way to generate the atrial model with non-uniform wall thickness is to perform mesh thickening (for non-ablation areas) using level-set thresholding from the patient's atria images.

If tissue fibrosis (e.g., scar tissue) can be identified in the medical images, this information is also included in the patient-specific anatomical LA model. For example, scar tissue and border zone tissue can be segmented using DE-MRI image data. The 3D anatomical model of the LA can be rigidly registered on a DE-MRI image using the coordinates of the MR scanner plus correlations between image information in the DE-MRI image and the 3D anatomical model. An expectation-minimization algorithm with belief prior and spatial regularization can then be employed to segment the scar and border zone tissue. This method works on in-vivo, multi-modality images and adds smoothing constraints for increased robustness to noise. Healthy tissue and scar tissue are modeled using a Gaussian mixture model with two modes. Given a three-class segmentation, the parameters of the mixture model are estimated, from which a belief value $\lambda$ is derived. Voxels with $\lambda<0.5$ are rejected from the model and classified as border zone. The border zone is a zone surrounding the scar tissue that represents healing tissue. For increased robustness and regularity, Markov random fields are employed to reject voxels according to the state of neighboring voxels. Furthermore, voxels farther than N-mm from the current scar estimate are never rejected, assuming that border zone can only be found in the proximity of scars. A graph-cut algorithm may be employed to estimate smooth interfaces between tissue types. The graph-cut algorithm is initialized with a coarse classification obtained using a k-means algorithm or similar algorithm and is iterated until convergence (e.g., when the parameters of the mixture model do not change anymore). The segmented scar tissue and surrounding border zone is then mapped to the volumetric mesh representation of the LA.

Returning to FIG. 1, at step 106, derived metrics for the LA and the LAA are computed using a patient-specific computational model of heart function based on the LA and LAA measurements extracted in step 104. The computational model of heart function may include modeling of wall mechanics and electrical signal propagation in a fully-coupled or de-coupled manner. In an advantageous embodiment, described in greater detail below, a patient-specific computational EP model can utilize the Lattice-Boltzmann method for electrophysiology (LBM-EP) to simulate electrical signal propagation in the LA. This can be done using the full heart, just the left heart (i.e., LA and left ventricle), just the atria (i.e., the LA and right atria), or just the LA. If the anatomical model generated in step 104 is comprised of less than the full heart, reduced-dimensionality models can be used for the missing anatomical components in order to enable the EP computation. Pathological EP conditions like atrial fibrillation can be included in the patient-specific computational model and used to generate the associated pathological wall kinematics, which can be used in the risk score prediction of step 108. In addition, simulated EP values, such as electrical activation time and action potential duration, can be computed for each point in the LA and LAA using the patient-specific computational EP model, and derived EP parameters can be computed based on the simulated EP values. Exemplary derived EP parameters can include chaotic depolarization patterns and sustained presence of rotors. In a possible implementation, the simulated EP values can be used to generate a simulated ECG signal for the patient, and derived features such as coarse fibrillatory waves, atrial flutter, and/or multifocal atrial tachycardia (MAT) can be extracted from the simulated ECG signal. The simulated EP values and/or the derived EP parameters can be input as features for machine learning based risk score prediction in step 108.

The patient-specific computational EP model is a computational model of LA electrophysiology, which is personalized by estimating patient-specific parameters of the computational EP model representing tissue properties of the LA tissue based on the measured EP data of the patient. The patient-specific computational EP model of the LA simulates electrical signal propagation in the LA. According to an advantageous implementation, the computational EP model uses the Lattice-Boltzmann method for electrophysiology (LBM-EP) to solve a monodomain tissue model over the patient-specific LA anatomy, using a multi-cellular model. In this method, a Cartesian grid domain for electrophysiology computations is calculated using the patient-specific anatomical model of the LA. A Cartesian grid, with uniform grid spacing or possibly with unequal and spatially varying spacing, is first generated in a bounding box surrounding the anatomical model of the LA. Grid spacing can be defined by the user or fixed in the system. A level-set representation is then calculated from the patient-specific anatomical model as follows. For every node x of the grid, the shortest distance to the anatomical model mesh is calculated, and assigned to that node. In an advantageous embodiment, nodes inside the myocardium are defined by positive distances, and nodes not inside the myocardium are defined by negative distances. The opposite convention can be utilized as well without any modification. Nodes at myocardium, endocardia, and epicardium are tagged as such, as well as other nodes pertaining to the atrial anatomical structures important to the conduction of atrial excitation. For example, the nodes of the patient-specific anatomical model on the Cartesian grid corresponding to the SA, BB, crista terminalis, pectinate muscles, and appendages can be tagged. Available scars and border zones are also reported in the domain through additional level-set information and the conductivity for such regions can be set to a predetermined reduced value or to zero. Fiber orientation f(x) is mapped to each node using rasterization techniques or is recomputed from the mapped endocardial and epicardial zones directly. Cell model parameters, such as the ionic current conductance c(x), are assigned to each node x.

The computational EP model of the LA calculates the transmembrane potential at each node within the LA using the Lattice-Boltzmann Method for Electrophysiology (LBM-EP). The computational EP model calculates the variation of the transmembrane potential $v(x,t)$ over time according to the mono-domain equation:

$$\frac{dv(x, t)}{dt} = R(x, t) + \nabla \cdot c(x)D(x)\nabla v(x, t), \quad (1)$$

where $R(x,t)$ is a reaction term describing the cellular mechanisms giving rise to the action potential, $c(x)$ is the local ionic current conductance, $D(x)$ is the anisotropy (transverse isotropy) matrix defined by $(1-\rho)f(x)f(x)^T + \rho \text{Id}$, $\rho$ being the ratio between the cross-fiber diffusivity and the fiber diffusivity (typically $\rho=0.11$-$0.25$). It is also possible to use fully isotropic tensors $D(x)$ for improved characterization of the atrial fiber architecture.

The choice of the reaction term $R(x,t)$ depends on the cellular model of cardiac electrophysiology that is used. According to an advantageous embodiment of the present invention, a multi-cell EP model can be used to model the EP of the atria. In order to describe the effect of non-homogeneity of the tissue on the atrial EP, the Cartesian nodes in the computational domain of the LBM-EP solver pertaining to the various atrial anatomical structures can be tagged and assigned with different cellular models and/or electrical conductivity values. In an exemplary implementation, the Courtemanche-Ramirez-Nattel (CRN) human atrial cell model, described in Courtemanche et al., "Ionic Mechanisms Underlying Human Atrial Action Potential Properties: Insights from a Mathematical Model", *Am. J. Physiol.* 275, H301-H321 (1998), can be used as the atrial cell mode. The CRN atrial cell model features 35 static parameters and 21 ordinary differential equations to describe 12 ionic channels, the corresponding gating variables and ionic concentrations.

Equation (1) is solved using the Lattice-Boltzmann method for electrophysiology, referred to herein as LBM-EP. LBM-EP is a highly parallelizable algorithm to solve monodomain electrophysiology equations. The LBM-EP algorithm is described in greater detail in United States Published Patent Application No. 2013/0226542, entitled "Method and System for Fast Patient-Specific Cardiac Electrophysiology Simulations for Therapy Planning and Guidance", which is incorporated herein by reference in its entirety. Contrary to standard finite-element methods, LBM-EP does not explicitly solve the reaction-diffusion equation but rather computes the "movement" of particles on a Cartesian grid, from which the reaction-diffusion behavior emerges. The particles can move according to fixed directions (or connectivities), with a certain probability. The algorithm includes two node-wise steps: streaming, which makes the particle jump from one node to another; and collision, which takes care of mass preservation and boundary conditions. It can be mathematically shown that this simple algorithm reproduces dynamics of the reaction-diffusion equation. In order to compute the cardiac electrophysiology using LBM-EP, domain boundaries are represented as level-sets and tissue anisotropy is modeled. In sinus rhythm, the electrocardiography model can be computed with periodic stimulus at the septum to mimic the fast conducting His bundle.

Since the LBM-EP method is completely node-wise and the time-integration is explicit, the computations can be done locally and the method is therefore easily adapted to highly parallel architectures. In an advantageous embodiment, the method can be implemented on one or more general purpose graphics processing units (GPGPU), which enables near real-time and accurate cardiac electrophysiology computation during the intervention. In this embodiment, this method can be optimized to fully benefit from the computational power of GPGPUs. For example, adaptive computational block aggregation can be performed to balance between computational power and memory bandwidth. Adaptive time-stepping methods can also be implemented to take into account the current EP dynamics, in particular in sinus rhythm regions. For example, small time steps can be used when the fast front propagation is occurring, larger time steps can be used during the refractory period, and even larger time steps can be used during the depolarization state. Adaptive mesh refinement techniques can also be implemented to reduce the overall computational effort in the presence of thick-walled structures (e.g., ventricles) and thin-walled structures (e.g., atria). The model can be interfaced with model repositories for greater flexibility.

The computational EP model of the LA can be coupled with a boundary element model of potential propagation in soft tissue in order to calculate an ECG resulting from the simulated cardiac electrophysiology. This allows body surface ECG measurements of the patient to be back-mapped to the atrial model for personalization of the computation EP model. The computational EP model of the atria computes a transmembrane potential for each node of the patient-specific anatomical model on the computational domain at each time step. An extra-cellular potential $\phi_e$ is calculated at each node of the computational domain based on the transmembrane potential $v(x,t)$ using a closed-form expression ($\Omega$ defines the computational domain; $|\Omega|$ is the number of elements therein):

$$\phi_e(x, t) = \frac{\lambda}{1+\lambda} \frac{1}{|\Omega|} \int_\Omega [v(y, t) - v(x, t)] dy, \quad (2)$$

where $\lambda$ is a constant diffusion anisotropy ratio, $\lambda = D_i(x)/D_e(x)$, and $D_i$ and $D_e$ are intra- and extra-cellular diffusivity tensors, respectively. The extra-cellular potential $\phi_e$ is then mapped back to the atria surface mesh using tri-linear interpolation. The extra-cellular potentials are then projected onto a torso surface mesh using a boundary element method (BEM). The potential $\phi(x)$ at any point x of the thoracic domain (torso surface mesh) can be calculated as:

$$\phi(x) = \frac{1}{4\pi} \int_{S_B} \phi_b \frac{r \cdot n}{\|r\|^3} dS_B - \frac{1}{4\pi} \int_{S_H} \left[ \phi_e \frac{r \cdot n}{\|r\|^3} + \frac{\nabla \phi_e \cdot n}{\|r\|} \right] dS_H, \quad (3)$$

where r is the vector defined by x and the integration point n, while $S_B$ and $S_H$ are the torso and epicardium surfaces, respectively. The body surface potential at the torso, $\phi_b$, can be expressed as a function of the extra-cellular potential $\phi_e$, which allows the potential to be calculated at any point on the torso. The torso mesh can be segmented from the medical image data using machine learning algorithms. According to a possible implementation, the body surface potential $\phi_b$ can be calculated for each vertex on the torso mesh. In another possible implementation, the body surface potential $\phi_b$ may be calculated only for vertices on the torso mesh corresponding to the locations of leads used to acquire the measured ECG signals (e.g., 12 lead ECG) of the patient. A simulated ECG signal is calculated using the body surface potentials calculated at the ECG lead positions, and ECG features, such as the duration of the QRS complex $\Delta_{QRS}$ and the electrical axis angle $\alpha_{EA}$ can be derived automatically from the simulated ECG signal. It should be noted that in the above description a homogeneous torso model is employed.

However, this can be extended to a heterogeneous torso model that incorporates muscle, lungs, bones, fat and other tissues, as identified in medical images. Each tissue would then have different electrical conductivity.

The computational EP model of the LA needs to be personalized in order to be predictive for a specific patient. The computational EP model of the LA is personalized based on EP measurements of the patient, such as invasive cardiac EP maps or body surface potential maps. In an exemplary embodiment, the electrophysiology (EP) data of the patient is first fused with the patient-specific anatomical model of the atria. The EP data of the patient can include invasive cardiac EP maps acquired for the patient and/or body surface potential measurements. Body surface potential measurements are measurements of electrical potentials on the torso of the patient and can refer to body surface potential maps acquired using body surface mapping (BSM) or ECG measurements of the patient using ECG leads on a patient's torso (e.g., 12 lead ECG measurements). Invasive cardiac maps are generated invasively by measuring potentials at various points in the heart over time, for example using a catheter mapping system or a catheter basket system. In order to personalize the computational EP model using invasive cardiac EP maps, the cardiac EP data is registered to the patient-specific anatomical model of the atria.

In order to fuse body surface potential measurements (e.g., body surface potential maps acquired using BSM or ECG measurements) to the patient-specific anatomical model of the atria, the body surface measurements are mapped to a patient-specific torso model that is registered to the patient-specific anatomical model of the atria. A 3D image of the patient's torso can be acquired, for example at the beginning of the intervention, and a triangulated mesh of the patient's torso can be segmented from the 3D image using a segmentation algorithm, such as graph cuts. In a case in which 3D torso images cannot be acquired, 2D MRI scout images can used to generate a torso model. In this case, contours of the visible torso in the 2D scout images can be automatically extracted, for example using graph-cuts. A stored 3D torso atlas can then be registered based on the 2D scout images using an affine transformation to match the torso contours extracted from the 2D scout images. This registration algorithm leverages the scout image positions (axial, sagittal and coronal) for increased robustness and minimizes risks of local minima. Once the torso is modeled, the patient-specific torso model can be automatically registered to the heart model using the scanner coordinates. Lead positions from which the body surface potentials were measured are mapped to the torso model. For example the lead positions can be mapped automatically or using user-defined landmarks. The body surface potential measurements can then be back-projected to the patient-specific anatomical model of the torso.

Once the patient-specific torso model is registered to the patient-specific anatomical model of the atria, an electrical model of diffusion in the torso can be used to describe the coupling relationship between the heart and the torso. As described above, electrical potentials on the torso can be calculated from cardiac potentials by first inferring extracellular potentials from transmembrane potentials on the atrium, and then solving a Poisson equation using the boundary element method (BEM). The electrical coupling between the heart mesh and the torso mesh can be modeled by the linear relationship $\forall t, Y_t = T^* X_t$, where $X_t(x)$ denotes the extra-cellular potentials on the epicardium, $Y_t(x)$ denotes the torso potentials, and T is the coupling matrix obtained by boundary element discretization of the heart-torso geometry and solving the Poisson equation for electrical potentials.

The EP measurements of the patient are used to personalize the electrical conductivity values and multi-cell model parameters at the nodes of the computational domain. For a detailed multi-cell model specific for the atria, such as the CRN atrial cell model which has 35 parameters, a model reduction approach can be used to reduce the computational cost and number of model parameters. For example, a reduced model can be constructed by action potential (AP) manifold learning to reduce the number model parameters followed by learning a regression model to predict the parameters in the reduce AP manifold. This speeds up the personalization procedure, because the more parameters to be estimated, the larger number of iterations needed for the forward solver.

In one embodiment, the personalization of the computational EP model can be performed using an inverse problem approach based on a comparison of simulated EP data generated by performing simulations using the computational EP model and the EP measurements of the patient. In particular, the personalization can be formulated as an optimization problem with the goal of minimizing the point-wise difference between the calculated (simulated) activation times using the computational EP model and the activation times in the measured EP data of the patient over all the nodes of the computational domain (i.e., over all the nodes of the patient-specific anatomical model of the atria). For increased estimation convergence and robustness to local minima, a coarse-to-fine strategy can be employed. In the coarse-to-fine strategy, a parameter value (e.g., electrical conductivity c) is first estimated for the whole LA. Areas with larger errors are then partitioned, and one parameter value per partition is estimated, initialized to the value of the previous step. The procedure is then iterated until convergence.

In another embodiment, machine learning methods can be utilized to estimate personalized parameters of the computational EP model of the LA based on the EP measurements of the patient. In an offline training stage, a large database of activation maps or other EP measurements are created using the computational EP model with different parameter values. Advanced non-linear manifold learning techniques are utilized to train a regression function, and the personalized parameters are estimated on-line by applying the trained regression function to regress the local values of electrical conductivities and multi-cell model parameters given the local activation maps of the measured EP data of the patient.

Figure 4:
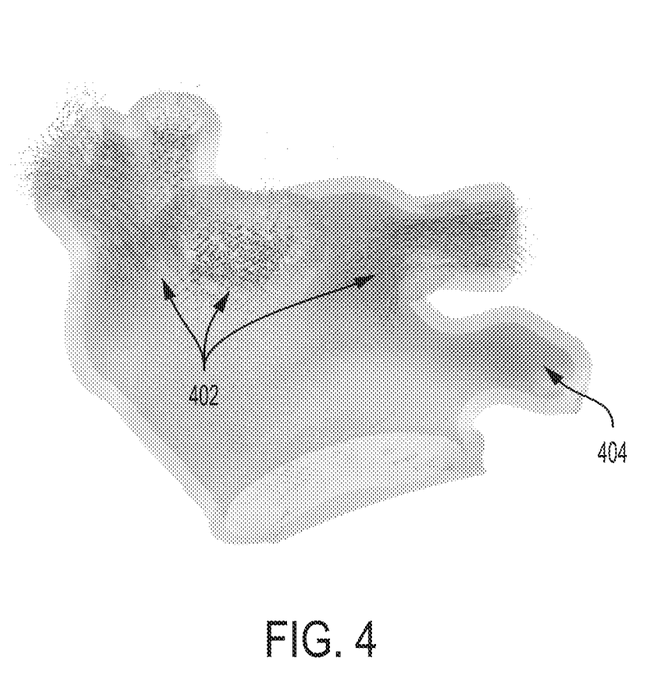
FIG. 4 illustrates an example of simulated blood flow in the LA.

The computational model of heart function may also include modeling of blood flow. The modeling/simulation of blood flow in the LA can be performed using Computational Fluid Dynamics (CFD) inside a domain whose boundary is given by the segmented LA mesh. The computational domain can be static or dynamic. For a static domain, zero velocity (corresponding to no-slip) boundary conditions can be imposed on the LA wall. For a dynamic domain, the coupling between the LA wall and the fluid domain (blood flow) can be implemented using Fluid Structure Interaction (FSI) framework. The FSI coupling between the LA wall and the blood flow can be performed using 1-way FSI, in which the motion of the wall is prescribed beforehand (e.g., based on observed wall motion in 4D (3D+time) medical image data) for every time step, and non-slip velocity boundary conditions force the fluid (blood) to move with the prescribed wall velocity. Such a method is described in greater detail in U.S. Pat. No. 8,682,626, entitled "Method and System for Comprehensive Patient-Specific Modeling of the Heart", which is incorporated herein by reference in its entirety. Alternatively, a 2-way FSI formulation can be used, in which the wall is modeled as a deformable material, endowed with material properties corresponding to atrial tissue, and force and/or velocity information are exchanged at the wall between the tissue and blood. An exemplary way to implement such a formulation is to use liquid pressure to generate traction force boundary conditions for the deformable solid, and to use the position and kinematics of the solid wall as boundary conditions for the fluid (blood). The CFD can simulate the blood flow in the LA using the standard Navier-Stokes equations for momentum and mass conservation, or from alternative formulations like the Lattice-Boltzmann method (LBM). FIG. 4 illustrates an example of simulated blood flow in the LA. In particular, FIG. 4 shows blood velocity vectors 402 obtained from CFD computations in the LA. Reduced circulation inside the LAA 404 can be observed in the simulated blood flow shown in FIG. 4.

Figure 5:
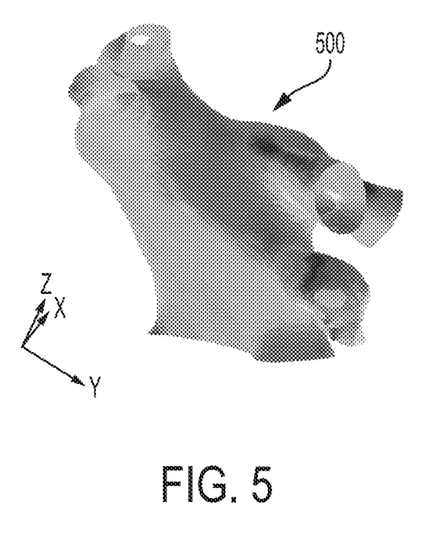
FIG. 5 illustrates an exemplary feature map in which a hemodynamic feature field is visualized on the surface of the LA.

According to an advantageous embodiment of the present invention, the patient-specific computational model of heart function is used to perform a generative analysis (i.e., to generate features) of the hemodynamics specific to LA and to the LAA in particular. This can include statistical characterization (e.g., mean) of primary hemodynamic variables, such as blood velocity and pressure, and/or derived parameters particular to the LA and/or LAA. Derived parameters refer to parameters or indices calculated from the computed/simulated hemodynamics. Examples of derived parameters/indices can be related directly to hemodynamic indices, energy or pressure indices, or specific LAA flow indices. Hemodynamic indices can include wall-shear stress (WSS)-based indices in the LA or, in a possible implementation, only in the LAA, (e.g., temporally averaged, spatial mean WSS (TASMWSS), temporally averaged, spatial maximum WSS, temporally averaged, spatial 99th percentile WSS), low wall shear area (LSA), low shear concentration index (LSCI), low shear index (LSI), high shear area (HSA), SCI (=TASMWSS in HSA/TASMWSS in LAA), mean, maximum and 99th percentile WSS spatial gradient (WSSG), and/or mean oscillatory shear index (OSI). Energy and pressure related indices can include energy loss in the LAA, pressure loss coefficient of the LAA, kinetic energy ratio (KER), and/or viscous dissipation ratio (VDR). Other more specific LAA flow indices can include the relative residence time (RRT), inflow concentration index (ICI), and/or vortex length (VL). The statistical characterization of the primary hemodynamic parameters (e.g., mean velocity and/or mean pressure) and the derived parameters can be computed for each point on the segmented LA mesh based on a hemodynamics simulation over a time period (e.g., a cardiac cycle). Such hemodynamic features can then be mapped over the surface of the segmented LA, as shown in FIG. 5. FIG. 5 illustrates an exemplary feature map 500 in which a hemodynamic feature field is visualized on the surface of the LA. Such a feature field can be enhanced on the LAA. EP features, such as activation time and action potential duration, computed using the computational EP model can also be computed for each point of the segmented LA mesh.

Returning to FIG. 1, at step 108, a risk score predicting a risk of ischemic (embolic) stroke is calculated based on the measurements of the LA and LAA extracted from the medical image data and the metrics computed using the computational model of heart function. The LA and LAA measurements extracted from the medical image data in step 104 and the LA and LAA metrics computed using the computational model of heart function in step 106 are used as features and a machine learning based method is used to calculate a stroke risk score based on those features. In an exemplary embodiment, deep learning may be used to train a deep neural network that learns a mapping from the input features to a stroke risk score for the patient. The deep neural network is trained in an offline training phase based on a database of training images and ground-truth values. For a specific patient, measured features (e.g., morphological features) extracted from the medical image data and computational features (e.g., hemodynamic features and EP features) computed using the computation model of heart function are input to the trained deep neural network, and the trained deep neural network calculates a stroke risk score for the patient based on the input features. It is to be understood that the present invention is not limited to deep learning, and other types of machine learning may be used as well.

The measured features input to the trained machine learning based classifier can include morphological (anatomical) features including but not limited to LV volume, LAA volume, and number of LAA lobes. The measured features may also include hemodynamics measurements extracted from the medical image data, such as velocity measurements and a left ventricle ejection fraction (LVEF) measurement, and EP measurements of the patient. The degree of dense spontaneous echo contrast (SEC) may also be measured in the medical image data and input as a feature. The computed features can include simulated hemodynamic features, such as statistical characterizations of hemodynamic parameters (e.g., blood velocity and pressure) and derived metrics including derived hemodynamic indices, energy and pressure related indices, and other more specific LAA related flow indices described above. Each of the hemodynamic features can be input for all mesh points in the LA or for all mesh points in the LAA. The computed features can also include simulated EP features, such as electrical activation time and action potential duration for all points in the LA or all points in the LAA, as well as derived EP features, such as chaotic depolarization patterns and sustained presence of rotors, coarse fibrillatory waves, atrial flutter, and/or multifocal atrial tachycardia (MAT). Machine learning based techniques, such as deep learning, can be used to automate encoding of "hidden" parameters associated with the feature list. In addition, traditional clinical risk factors, such as the CHADS2 score, may be calculated for the patient and input as a feature to the trained machine learning based classifier. Alternatively, the trained machine learning based classifier may calculate a risk score without the traditional clinical risk score, and the risk score calculated by the trained machine learning based classifier can be combined with the traditional risk score (e.g., CHADS2 score), resulting in a composite risk score.

In an advantageous embodiment, molecular information can also be included in the feature list for the machine learning based calculation of the stroke risk score. For example, a feature can be added that indicates the presence of transforming growth factor beta 1 (tgf-beta1), which has been documented to increase vulnerability to Afib. In an advantageous embodiment, drug information for a patient can also be included in the feature list for the machine learning based calculation of the stroke risk score.

At step 110, the stroke risk score and visualizations of extracted and derived data are output. The risk score for the patient is calculated by the trained machine learning based classifier, and output, for example by displaying the risk score on a display of a computer system and storing the risk score for the patient in a memory or storage of a computer system. In addition one or more relevant features/metrics can be visualized and displayed on a display of a computer system. For example, a 3D view of stagnations (e.g., high RRT) regions within the LA can be visualized by mapping a color map corresponding to computed RRT values to the extracted 3D anatomical model of the LA and displaying LA model with the color map on a display device. Other features can be similarly displayed as well.

In an embodiment of the present invention, the method of FIG. 1 can be used to plan and test the efficacy of various treatments to see if the treatments reduce the patient's risk of stroke. For example, the method of FIG. 1 can be used to calculate an initial stroke risk score for the patient. The computational model of heart function can then be used to simulate various Afib treatment procedures, such as pulmonary vein catheter isolation, and then re-compute the simulated heart function, and computed updated features, from which updated risk scores can be calculated. The updated risk scores can be compared to the initial stroke risk score to determine if the Afib treatments that were simulated would reduce the patient's risk of stroke. Additional details regarding simulating Afib treatments using a computational EP model of the atria are described in United States Patent Application Publication No. 2016/0058520, which is incorporated herein by reference in its entirety. Similarly, the computational model can also be used to test the effect of various LAA closure devices or various ablation therapies on the stroke risk score of the patient. The computational model can also be extended to address other sources of thrombus formation in the heart, which can influence decisions related, for example, to valve device therapy, etc.

Figure 6:
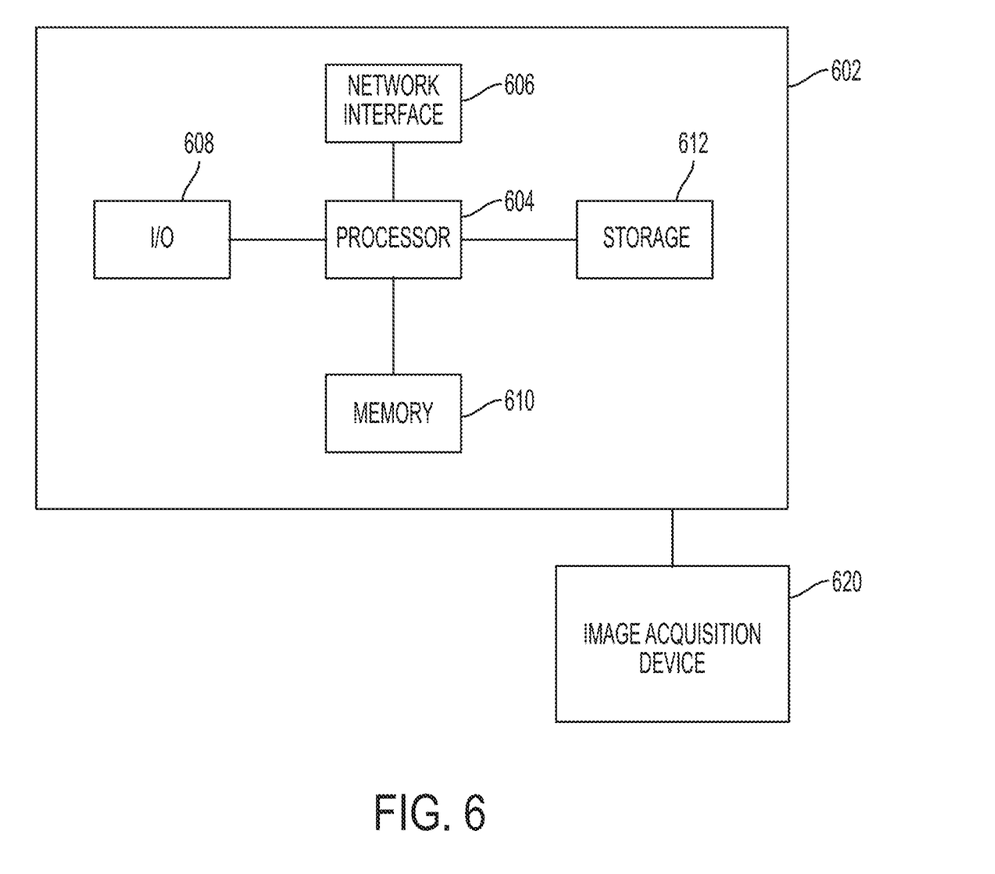
FIG. 6 is a high-level block diagram of a computer capable of implementing the present invention.

The above-described methods for patient-specific ischemic stroke risk prediction can be implemented on a computer using well-known computer processors, memory units, storage devices, computer software, and other components. A high-level block diagram of such a computer is illustrated in FIG. 6. Computer 602 contains a processor 604, which controls the overall operation of the computer 602 by executing computer program instructions which define such operation. The computer program instructions may be stored in a storage device 612 (e.g., magnetic disk) and loaded into memory 610 when execution of the computer program instructions is desired. Thus, the steps of the method of FIG. 1 may be defined by the computer program instructions stored in the memory 610 and/or storage 612 and controlled by the processor 604 executing the computer program instructions. An image acquisition device 620, such as a CT scanning device, C-arm image acquisition device, MR scanning device, Ultrasound device, etc., can be connected to the computer 602 to input image data to the computer 602. It is possible to implement the image acquisition device 620 and the computer 602 as one device. It is also possible that the image acquisition device 620 and the computer 602 communicate wirelessly through a network. In a possible embodiment, the computer 602 may be located remotely with respect to the image acquisition device 620 and may perform the method steps as part of a server or cloud based service. The computer 602 also includes one or more network interfaces 606 for communicating with other devices via a network. The computer 602 also includes other input/output devices 608 that enable user interaction with the computer 602 (e.g., display, keyboard, mouse, speakers, buttons, etc.). Such input/output devices 608 may be used in conjunction with a set of computer programs as an annotation tool to annotate volumes received from the image acquisition device 620. One skilled in the art will recognize that an implementation of an actual computer could contain other components as well, and that FIG. 6 is a high level representation of some of the components of such a computer for illustrative purposes.

The above-described methods for medical image synthesis may be implemented using computers operating in a client-server relationship. Typically, in such a system, the client computers are located remotely from the server computer and interact via a network. The client-server relationship may be defined and controlled by computer programs running on the respective client and server computers.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for medical image based patient-specific stroke risk prediction, comprising:
    extracting left atrium (LA) and left atrium appendage (LAA) measurements from medical image data of a patient;
    computing derived metrics for the LA and LAA of the patient using a patient-specific computational model of cardiac function based on the LA and LAA measurements extracted from the medical image data of the patient; and
    calculating a stroke risk score for the patient based on the extracted LA and LAA measurements and the computed derived metrics for the LA and LAA of the patient using a trained machine learning based classifier, wherein the extracted LA and LAA measurements and the computed derived metrics for the LA and LAA are input as features to the trained machine learning based classifier and the trained machine learning based classifier maps the extracted LA and LAA measurements and the computed derived metrics for the LA and LAA to the stroke risk score.

2. The method of claim 1, wherein extracting left atrium (LA) and left atrium appendage measurements from medical image data of a patient comprises:
    segmenting the LA in the medical image data of the patient.

3. The method of claim 2, wherein segmenting the LA in the medical image data of the patient comprises:
    generating a 3D LA mesh from 3D medical image data of the patient.

4. The method of claim 3, wherein generating a 3D LA mesh from 3D medical image data of the patient comprises:
    segmenting a plurality of LA parts in the medical image data using a multi-part atria model; and
    generating a consolidated LA mesh from the segmented plurality of LA parts.

5. The method of claim 2, wherein segmenting the LA in the medical image data of the patient comprises:
    generating a sequence of LA meshes from 4D (3D+time) medical image data of the patient.

6. The method of claim 2, wherein extracting left atrium (LA) and left atrium appendage measurements from medical image data of a patient further comprises:

extracting an LA volume, LAA volume, and a number of LAA lobes based on the segmented LA, wherein the LA volume, LAA volume, and number of LAA lobes are input as features to the machine learning based classifier.

7. The method of claim 2, wherein extracting left atrium (LA) and left atrium appendage measurements from medical image data of a patient further comprises:
extracting hemodynamic measurements for the LA and LAA from the medical image data of the patient.

8. The method of claim 1, wherein computing derived metrics for the LA and LAA of the patient using a patient-specific computational model of cardiac function based on the LA and LAA measurements extracted from the medical image data of the patient comprises:
simulating blood flow in the LA and LAA using the patient-specific computational model of cardiac function; and
computing hemodynamic features for the LA and LAA based on the simulated blood flow in the LA and LAA, wherein the hemodynamic features are input to the trained machine learning based classifier.

9. The method of claim 8, wherein computing hemodynamic features for the LA and LAA based on the simulated blood flow in the LA and LAA comprises:
computing derived hemodynamic parameters for at least a plurality of locations in the LAA based on the simulated blood flow in the LA and LAA, wherein the derived hemodynamic parameters include one or more of relative residence time (RRT), energy loss, pressure loss coefficient, wall-shear stress (WSS), or oscillatory index (OSI).

10. The method of claim 8, wherein computing hemodynamic features for the LA and LAA based on the simulated blood flow in the LA and LAA comprises:
computing for at least a plurality of locations in the LAA, a statistical characterization of at least one of blood flow velocity or pressure based on the simulated blood flow in the LA and LAA.

11. The method of claim 8, wherein computing derived metrics for the LA and LAA of the patient using a patient-specific computational model of cardiac function based on the LA and LAA measurements extracted from the medical image data of the patient further comprises:
simulating electrical signal propagation in the LA using the patient-specific computational model of cardiac function; and
computing electrophysiological features for the LA and LAA from the simulated electrical signal propagation in the LA, wherein the computed electrophysiological features are input as features to the machine learning based classifier.

12. The method of claim 1, wherein the extracted LA and LAA measurements input as features to the machine learning based classifier include LA volume, LAA volume, and number of LAA lobes, and the computed derived metrics input as features to the machine learning based classifier include one or more of relative residence time (RRT), energy loss, pressure loss coefficient, wall-shear stress (WSS), oscillatory index (OSI), mean blood flow velocity, or mean blood pressure, at one or more points in the LA and LAA.

13. The method of claim 1, wherein calculating a stroke risk score of the patient based on the extracted LA and LAA measurements and the computed derived metrics for the LA and LAA of the patient using a trained machine learning based classifier comprises:
calculating the stroke risk score of the patient based on the extracted LA and LAA measurements and the computed derived metrics for the LA and LAA of the patient using a trained deep neural network.

14. An apparatus for medical image based patient-specific stroke risk prediction, comprising:
means for extracting left atrium (LA) and left atrium appendage (LAA) measurements from medical image data of a patient;
means for computing derived metrics for the LA and LAA of the patient using a patient-specific computational model of cardiac function based on the LA and LAA measurements extracted from the medical image data of the patient; and
means for calculating a stroke risk score for the patient based on the extracted LA and LAA measurements and the computed derived metrics for the LA and LAA of the patient using a trained machine learning based classifier, wherein the extracted LA and LAA measurements and the computed derived metrics for the LA and LAA are input as features to the trained machine learning based classifier and the trained machine learning based classifier maps the extracted LA and LAA measurements and the computed derived metrics for the LA and LAA to the stroke risk score.

15. The apparatus of claim 14, wherein the means for extracting left atrium (LA) and left atrium appendage measurements from medical image data of a patient comprises:
means for segmenting the LA in the medical image data of the patient.

16. The apparatus of claim 15, wherein the left atrium (LA) and left atrium appendage measurements input as features to the trained machine learning based classifier include an LA volume, LAA volume, and a number of LAA lobes determined based on the segmented LA.

17. The apparatus of claim 15, wherein the means for extracting left atrium (LA) and left atrium appendage measurements from medical image data of a patient further comprises:
means for extracting hemodynamic measurements for the LA and LAA from the medical image data of the patient.

18. The apparatus of claim 14, wherein the means for computing derived metrics for the LA and LAA of the patient using a patient-specific computational model of cardiac function based on the LA and LAA measurements extracted from the medical image data of the patient comprises:
means for simulating blood flow in the LA and LAA using the patient-specific computational model of cardiac function; and
means for computing hemodynamic features for the LA and LAA based on the simulated blood flow in the LA and LAA, wherein the hemodynamic features are input to the trained machine learning based classifier.

19. The apparatus of claim 18, wherein the means for computing hemodynamic features for the LA and LAA based on the simulated blood flow in the LA and LAA comprises:
means for computing derived hemodynamic parameters for at least a plurality of locations in the LAA based on the simulated blood flow in the LA and LAA, wherein the derived hemodynamic parameters include one or more of relative residence time (RRT), energy loss, pressure loss coefficient, wall-shear stress (WSS), or oscillatory index (OSI).

20. The apparatus of claim 18, wherein the means for computing hemodynamic features for the LA and LAA based on the simulated blood flow in the LA and LAA comprises:
    means for computing for at least a plurality of locations in the LAA, a statistical characterization of at least one of blood flow velocity or pressure based on the simulated blood flow in the LA and LAA.

21. The apparatus of claim 18, wherein the means for computing derived metrics for the LA and LAA of the patient using a patient-specific computational model of cardiac function based on the LA and LAA measurements extracted from the medical image data of the patient further comprises:
    means for simulating electrical signal propagation in the LA using the patient-specific computational model of cardiac function; and
    means for computing electrophysiological features for the LA and LAA from the simulated electrical signal propagation in the LA, wherein the computed electrophysiological features are input as features to the machine learning based classifier.

22. The apparatus of claim 14, wherein the extracted LA and LAA measurements input as features to the machine learning based classifier include LA volume, LAA volume, and number of LAA lobes, and the computed derived metrics input as features to the machine learning based classifier include one or more of relative residence time (RRT), energy loss, pressure loss coefficient, wall-shear stress (WSS), oscillatory index (OSI), mean blood flow velocity, or mean blood pressure, at one or more points in the LA and LAA.

23. A non-transitory computer readable medium storing computer program instructions for medical image based patient-specific stroke risk prediction, the computer program instructions when executed by a processor cause the processor to perform operations comprising:
    extracting left atrium (LA) and left atrium appendage (LAA) measurements from medical image data of a patient;
    computing derived metrics for the LA and LAA of the patient using a patient-specific computational model of cardiac function based on the LA and LAA measurements extracted from the medical image data of the patient; and
    calculating a stroke risk score for the patient based on the extracted LA and LAA measurements and the computed derived metrics for the LA and LAA of the patient using a trained machine learning based classifier, wherein the extracted LA and LAA measurements and the computed derived metrics for the LA and LAA are input as features to the trained machine learning based classifier and the trained machine learning based classifier maps the extracted LA and LAA measurements and the computed derived metrics for the LA and LAA to the stroke risk score.

24. The non-transitory computer readable medium of claim 23, wherein extracting left atrium (LA) and left atrium appendage measurements from medical image data of a patient comprises:
    segmenting the LA in the medical image data of the patient.

25. The non-transitory computer readable medium of claim 23, wherein extracting left atrium (LA) and left atrium appendage measurements from medical image data of a patient further comprises:
    extracting an LA volume, LAA volume, and a number of LAA lobes based on the segmented LA, wherein the LA volume, LAA volume, and number of LAA lobes are input as features to the machine learning based classifier.

26. The non-transitory computer readable medium of claim 23, wherein extracting left atrium (LA) and left atrium appendage measurements from medical image data of a patient further comprises:
    extracting hemodynamic measurements for the LA and LAA from the medical image data of the patient.

27. The non-transitory computer readable medium of claim 23, wherein computing derived metrics for the LA and LAA of the patient using a patient-specific computational model of cardiac function based on the LA and LAA measurements extracted from the medical image data of the patient comprises:
    simulating blood flow in the LA and LAA using the patient-specific computational model of cardiac function; and
    computing hemodynamic features for the LA and LAA based on the simulated blood flow in the LA and LAA, wherein the hemodynamic features are input to the trained machine learning based classifier.

28. The non-transitory computer readable medium of claim 27, wherein computing hemodynamic features for the LA and LAA based on the simulated blood flow in the LA and LAA comprises:
    computing derived hemodynamic parameters for at least a plurality of locations in the LAA based on the simulated blood flow in the LA and LAA, wherein the derived hemodynamic parameters include one or more of relative residence time (RRT), energy loss, pressure loss coefficient, wall-shear stress (WSS), or oscillatory index (OSI).

29. The non-transitory computer readable medium of claim 27, wherein computing hemodynamic features for the LA and LAA based on the simulated blood flow in the LA and LAA comprises:
    computing for at least a plurality of locations in the LAA, a statistical characterization of at least one of blood flow velocity or pressure based on the simulated blood flow in the LA and LAA.

30. The non-transitory computer readable medium of claim 27, wherein computing derived metrics for the LA and LAA of the patient using a patient-specific computational model of cardiac function based on the LA and LAA measurements extracted from the medical image data of the patient further comprises:
    simulating electrical signal propagation in the LA using the patient-specific computational model of cardiac function; and
    computing electrophysiological features for the LA and LAA from the simulated electrical signal propagation in the LA, wherein the computed electrophysiological features are input as features to the machine learning based classifier.

31. The non-transitory computer readable medium of claim 23, wherein the extracted LA and LAA measurements input as features to the machine learning based classifier include LA volume, LAA volume, and number of LAA lobes, and the computed derived metrics input as features to the machine learning based classifier include one or more of relative residence time (RRT), energy loss, pressure loss coefficient, wall-shear stress (WSS), oscillatory index (OSI), mean blood flow velocity, or mean blood pressure, at one or more points in the LA and LAA.

32. The non-transitory computer readable medium of claim 23, wherein calculating a stroke risk score of the patient based on the extracted LA and LAA measurements and the computed derived metrics for the LA and LAA of the patient using a trained machine learning based classifier comprises:
  calculating the stroke risk score of the patient based on the extracted LA and LAA measurements and the computed derived metrics for the LA and LAA of the patient using a trained deep neural network.

* * * * *